United States Patent [19]

Spinelli et al.

[11] Patent Number: 4,968,706
[45] Date of Patent: Nov. 6, 1990

[54] ETHERS AND THIOETHERS HAVING THERAPEUTICAL ACTIVITY, THEIR PREPARATION AND PHARMACEUTICAL COMPOSITIONS CONTAINING THEM

[75] Inventors: Silvano Spinelli; Roberto Di Domenico; Ernesto Menta; Bruno Lumachi; Licia Gallico; Sergio Tognella, all of Milan, Italy

[73] Assignee: Boehringer Mannhein Italia, S.p.A., Milan, Italy

[21] Appl. No.: 230,821

[22] Filed: Aug. 11, 1988

[30] Foreign Application Priority Data

Aug. 14, 1987 [IT] Italy ................................ 21657 A/87

[51] Int. Cl.⁵ .................. A61K 31/335; A61K 31/39; A61K 31/44; A61K 31/495; C07D 401/12; C07D 405/12; C07D 411/12; C07D 419/12; C07D 413/12

[52] U.S. Cl. ...................................... 514/336; 544/114; 544/121; 544/124; 544/139; 544/145; 544/148; 544/158; 544/159; 544/170; 544/171; 544/172; 544/174; 544/357; 544/360; 544/370; 544/374; 544/379; 544/384; 544/391; 546/194; 546/207; 546/210; 546/221; 546/222; 546/225; 546/226; 546/278; 546/283; 546/284; 546/334; 546/335; 514/467; 514/231.5; 514/231.8; 514/232.2; 514/235.5; 514/235.8; 514/237.5; 514/237.8; 514/238.2; 514/239.2; 514/252; 514/255; 514/277; 514/318; 514/326; 514/327; 514/330; 514/341; 514/357; 514/397; 514/400; 549/451; 549/452; 549/453; 549/454; 549/30; 548/336; 548/342; 548/344

[58] Field of Search ............... 549/451, 452, 453, 454; 546/283; 514/336, 467

[56] References Cited

U.S. PATENT DOCUMENTS 4,780,479 10/1988 Pickett et al. .................... 549/451

Primary Examiner—John M. Ford
Assistant Examiner—J. Richter
Attorney, Agent, or Firm—Armstrong, Nikaido, Marmelstein, Kubovcik & Murray

[57] ABSTRACT

Compounds of formula I

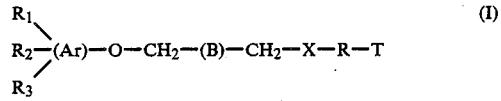

wherein Ar is an optionally substituted phenyl ring; B is a single bond, a group —($CH_2OCH_2$)$_n$— being n=1 or 2, a 2,4-disubstituted-1,3-dioxolane ring or a 2,4-disubstituted-1,3-thioxolane ring, R is a single bond, an optionally substituted methylene or ethylene group and T is 2-, 3- or 4-pyridyl, an optionally salified or esterified carboxy group or a carboxyamide group. Said compounds are useful in treatment of respiratory diseases.

8 Claims, No Drawings

ETHERS AND THIOETHERS HAVING THERAPEUTICAL ACTIVITY, THEIR PREPARATION AND PHARMACEUTICAL COMPOSITIONS CONTAINING THEM

The present invention concerns compounds endowed with mucolytic and antitussive activities.

The compounds of the invention have the following general formula I

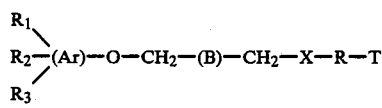

wherein:
- Ar is an unsubstituted or polysubstituted phenyl ring;
- B is selected in the group consisting of a valency bond, $-(CH_2O-CH_2)_n$, and 1,3-dioxolan-2,4-diyl or 1,3-thioxolan-2,4-diyl radical group which may be indifferently bonded to the remaining parts of the molecule by means of C(2) and C(4) carbons of the heterocyclic ring;
- X is sulphur or oxygen;
- T is a 2-, 3-or 4-pyridyl, carboxyl, $-CO_2R_6$, $-COR_6$, $-CO_2NH_2$, $-CONRdRe$, $-CO-NH-CH(Rc)-CO_2Ra$ or a di-$(C_1-C_4)$-alkylamino-$(C_1-C_4)$-alkylaminocarbonyl-, hydroxy, $(C_1-C_4)$-alkoxy-$(C_1-C_4)$-alkyl-aminocarbonyl-, di-$(C_1-C_4)$-alkyl-amino-$(C_1-C_4)$-alkoxy-$(C_1-C_4)$-alkyl -aminocarbonyl or 2-, 3-, 4-pyridylmethylamino -carbonyl group;
- R represents $-(CH_2)_n-$, $-CH(R_4)-$, $-CH_2-CH(NH_2)-$ or $-CH_2-CH(NH-CORa)-$ group;
- $R_1$, $R_2$ and $R_3$, that can be the same or different, are selected from the group consisting of hydrogen, hydroxy, $(C_1-C_5)$-acyloxy, $(C_1-C_4)$-alkyl, $(C_1-C_4)$-alkoxyl, $(C_2-C_4)$-alkenyl, halogen, $(C_1-C_5)$-acylamino, phenyl, phenoxy, imidazol-1-yl, carboxyl, $(C_1-C_3)$-alkoxy-carbonyl, carboxy-$(C_1-C_4)$-alkyl;
- $R_4$ is $(C_1-C_4)$-alkyl or a $(C_2-C_4)$-alkenyl group;
- Ra is hydrogen or a $(C_1-C_4)$ -alkyl group;
- $R_6$ is a $(C_1-C_6)$-alkyl group optionally substituted by $(C_1-C_6)$-alkoxy, carboxyl, $(C_1-C_4)$-alkylamino, di-$(C_1-C_4)$-alkylamino, morpholin-N-yl, piperidin-1-yl, 4-$(C_1-C_4)$-alkyl-piperazin-1-yl, $(C_3-C_6)$-alkenyl, phenyl or phenyl-$(C_1-C_6)$-alkyl groups;
- Rc is hydrogen or a $(C_1-C_6)$-alkyl, or $(C_6-C_{14})$-ar-$(C_1-C_4)$-alkyl, or heteroalkyl group of a residue of a natural α-aminoacid, and
- Rd and Re, which can be the same or different, are hydrogen, a $(C_1-C_6)$-alkyl optionally substituted by $(C_1-C_6)$-alkoxy, morpholin-N-yl, piperidin-1-yl, 4-$(C_1-C_4)$-alkyl-piperazin-1-yl, hydroxy-$(C_1-C_4)$-alkoxy-$(C_1-C_4)$-alkyl or di-$(C_1-C_4)$ -alkylamin -$(C_1-C_4)$-alkoxy-$(C_1-C_4)$-alkyl group or Rd and Re together with the nitrogen atom to which they are bonded form a heterocyclic ring selected from the group consisting of morpholin-N-yl, piperidin-1-yl and 4-$(C_1-C_4)$-alkyl-piperazin-1-yl.

In the scope of the invention are also included pharmaceutically acceptable salts, optical antipodes, i.e. the single enantiomers, mixtures of optical antipodes diasteroisomers and mixtures of diasteroisomers of compounds of formula I.

The above mentioned carboxy groups are optionally salified with an ammonium or alkaline cation.

The term halogen is to be understood to mean fluorine, chlorine, bromine and iodine, but preferably bromine and chlorine.

The aralkyl radical can be phenyl-$(C_1-C_4)$-alkyl or naphthyl-$(C_1-C_4)$-alkyl A $(C_1-C_6)$-alkyl, a $(C_6-C_{14})$-ar-$(C_1-C_4)$-alkyl and a heteroalkyl residue of a natural α-aminoacid means for example N-alanyl, N-valinyl, N-phenylalanyl, N-methionyl or N-histidinyl.

More particularly the present invention concerns addition salts with pharmaceutically acceptable bases, when in the compounds of formula I there is a free carboxylic group and addition salts with pharmaceutically acceptable acids, when in the compounds of formula I there is a basic organic portion.

Typical examples of non-toxic and pharmaceutically acceptable bases are organic bases, e.g. amines such as methylamine, dimethylamine, trimethylamine, ethylamine, diisopropylamine, N-methyl-N-hexylamine, tromethamine, cyclohexylamine, N-methyl-N-cyclohexylamine, α-phenylethylamine, β-phenylethylamine, N,N-dimethylethanolamine, N,N-dielhylethanolamine, ethylendiamine, piperidine, morpholine, piperazine, galactamine, N-methylglucamine, ephedrine, lysine, arginine and inorganic bases such as hydroxides of alkaline and alkaline-earth metals, as well as zinc and aluminum hydroxides.

Typical examples of non-toxic, pharmacologically acceptable acids are organic acids, such as acetic, formic, propionic, fumaric, tartaric, maleic, malic, malonic, benzoic, salicylic, 3,4,5-trimethoxybenzoic, methanesulphonic, benzenesulphonic, camphorsulphonic, lactic, aspartic, glutammic, L- or D-2-phenyl-thiazolidine-5-carboxylic acids, cystine and cysteine; and inorganic acids such as nitric, phosphoric, sulphuric, hydrochloric and hydrobromic acids.

According to the invention, alkyl, alkenyl, alkoxy groups may have linear or branched chain.

Non-limitative examples of compounds of the invention are those wherein the group

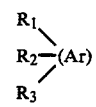

is phenyl, 2-hydroxyphenyl, 2- or 4-methoxyphenyl, 2-methoxy-4-allyl-phenyl, 3,4,5-trimethoxyphenyl, 3,5-dimethoxy-4-hydroxyphenyl, 3,5-ditert.butoxy-4-hydroxyphenyl, 4-acetamidophenyl, 4-ethoxycarbonylcarboxyamido-phenyl, 4-(imidazol-1-yl)-2-allyl-phenyl. B is a single bond or a 1,3-dioxolane-4,2-diyl, a 1,3-thioxolane-4,2-diyl, 1,3-thioxolane-2,4-diyl or a 1,3-dioxolane-2,4-diyl group of the formulae:

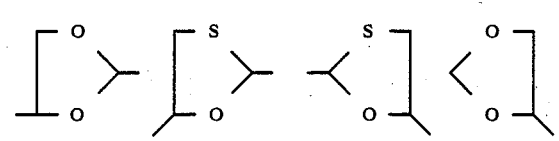

and X - R - T are one of the groups having the above reported formulae.

Particularly preferred examples of compounds of the invention are:

ethyl 4-/4-(2-methoxyphenoxy)-methyl-(E) (1,3)-dioxolane-2-yl/-3-oxa butanoate;
3-oxa-4-/4-(2-methoxyphenoxy)-methyl-(E)-(1,3) dioxolane-2-yl/-butanoic acid;
3-oxa-4-/4-(2-methoxyphenoxy)-methyl-(Z)-(1,3) dioxolane-2-yl/-butanoic acid;
3-oxa-4-/4-(2-methoxyphenoxy)-methyl-(Z,E) (1,3)-dioxolane-2-yl/-butanoic acid;
3-oxa-4-/4-(3,5-ditert.butyl-4-hydroxyphenoxy)methyl (Z,E)-(1,3)-dioxolane-2-yl/ -butanoic acid;
3-oxa-4-/-(3,5-dimethoxy-4-hydroxyphenoxy)methyl (Z,E)-(1,3)-dioxolane-2-yl/-butanoic acid;
3-oxa-4-/4-(3,4,5-trimethoxyphenoxy)methyl-(Z,E) (1,3)-dioxolane-2-yl/-butanoic acid;
3-oxa-4-/4-(2-methoxy-4-allyl-phenoxy)-methyl-(Z,E)-(1,3)-dioxolane-2-yl/-butanoic acid;
3-oxa-4-/4-(4-methoxyphenoxy)methyl-(Z,E)-(1,3)-dioxolane-2-yl/-butanoic acid;
3-thia-4-/4-(2-methoxyphenoxy)methyl-(Z,E)-dioxolane-2-yl/-butanoic acid;
3-thia-4-/4-(2-phenoxy)methyl-(Z)-(1,3)-dioxolane-2-yl/- butanoic acid;
3-thia-4-/4-(4-methoxyphenoxy)methyl-(Z,E)-(1,3)-dioxolane-2-yl/-butanoic acid;
3-thia-4-/4-(2-methoxyphenoxy)methyl-(E)-(1,3)-dioxolane-2-yl/-butanoic acid;
3-thia-4-/4-(2-hydroxyphenoxy)methyl-(Z,E)-(1,3)-dioxolane-2-yl/-butanoic acid;
3-thia-4-/4-(3,4,5-trimethoxyphenoxy)methyl-(Z,E)-1,3)-dioxolane-2-yl/-butanoic acid;
3-thia-4-/4-(3,5-dimethoxy-4-hydroxy-phenoxy)methyl-(Z,E)-(1,3)-dioxolane-2-Yl/-butanoic acid;
3-thia-4-/4-(4-imidazol-1-yl-phenoxy)-methyl-(Z,E)(1,3)-dioxolane-2-yl/-butanoic acid;
3-thia-4-/4-(3,5-ditert butyl-4-hydroxy-phenoxy)methyl (Z,E)-(1,3)-dioxolane-2-yl/-butanoic acid;
3-thia-4-/-4-(4-acetamidophenoxy)methyl-(Z,E)(1,3)-dioxolane-2-yl/-butanoic acid;
3-thia-4-/4-(2-methoxy-4-allyl-phenoxy)methyl-(Z,E)-(1,3)-dioxolane-2-yl/butanoic acid;
2-(acetylammino)-4-thia-5/4-(2-methoxyphenoxy) methyl(Z,E)-(1,3)-dioxolane-2-yl/-pentanoic acid;
2-(acetylamino)-4-thia-5/4-(4-methoxyphenoxy)methyl-(ZE)-(1,3)-dioxolane-2-yl/-pentanoic acid;
2S-/4-(2-methoxyphenoxy)methyl-(Z,E)-(1,3) dioxolane-2-yl/-methylthio-propionyl-glycine;
3-thia-4/4-(2-methoxyphenoxy)methyl-(Z,E)-(1,3)-thioxolane-2-yl/-butanoic acid;
3-thia-4/4-(4-methoxyphenoxy)-methyl-(Z,E)-(1,3)-thioxolane-2-yl/-butanoic acid;
3-thia-4/4-(3,4,5-trimethoxyphenoxy)methyl-(Z,E)-(1,3)-thioxolane-2-yl/-butanoic acid;
3-thia-4/4-(4-imidazol-1-yl)-phenoxy)methyl-(Z,E) -(1,3)-thioxolane-2-yl/-butanoic acid;
3-thia-4-/4-(4-acetamido-phenoxy)methyl-(Z,E)-(1,3)-thioxolane-2-yl/-butanoic acid;
2-acetylammino-4-thia-5-/4-(2-methoxyphenoxy) methyl-(Z,E)-(1,3)-thioxolane-2-yl/-pentanoic acid;
2-acetylammino-4-thia-5-/4-(4-methoxyphenoxy) methyl-(1,3)-thioxolane-2-yl/-pentanoic acid;
3-thia-4-/2-(2-methoxyphenoxy)methyl-(Z,E) (1,3)-dioxolane-4-yl/-butanoic acid;
methyl 2-(S)-acetylammino-4-thia-5-/2-(2-methoxy phenoxy)methyl-(Z,E)-(1,3)-dioxolane-4-yl/-pentanoate;
3-thia-5-(2-methoxyphenoxy)- pentanoic acid;
3-thia-5-(4-methoxyphenoxy)-pentanoic acid;
3-thia-5-(3,4,5-trimethoxyphenoxy)-pentanoic acid;
3-thia-5-(3,5-dimethoxy-4-hydroxy-phenoxy)-pentanoic acid;
3-thia-5-(3,5-ditert.butyl-4-hydroxy-phenoxy) pentanoic acid;
3-thia-5-(4-imidazol-i-yl-phenoxy)-pentanoic acid;
3-thia-5-(4-acetamido-phenoxy)-pentanoic acid;
3-thia-5-(2-methoxy-4-allyl-phenyl)-pentanoic acid;
1-(3-pyridyl-methylthio)methyl-4-(2-methoxyphenoxy)-methyl-(1,3)-dioxolane;
(Z,E)-2-(3-pyridyl-methylthio)-methyl-4 (2-methoxyphenoxy)methyl-(l,3)-dioxolane;
(Z,E)-4-(3-pyridyl-methylthio)-methyl-2 (2-methoxyphenoxy)methyl-(1,3)-dioxolane;
(Z,E)-2-(3-pyridyl-methylthio)-methyl-4 (methoxyphenoxy)methyl-(1,3)-dioxolane;
(Z,E)-2-(3-pyridyl-methylthio)-methyl-4-(2-methoxyphenoxy)-methyl-(1,3)-thioxolane:
1-(3-pyridyl)-2-thia-4(4-methoxyphenoxy)butane;
1-(3-pyridyl)-2-thia-4(-acetamido-phenoxy)butane;
1-(3-pyridyl)-2-thia-4-/4-(imidazol-1-yl)-phenoxy/butane;
1-(3-pyridyl)-2-thia-4-/2-methoxy-4-allyl-phenoxy/butane;
N-(3-pyridyl)-methy1,3-thia-4-/4-(2-methoxyphenoxy)-methyl-cis-trans-dioxolan-2-yl/-butanoic acid amide;
N-(3-pyridyl)methyl, 3-thia-5-(2-methoxyphenoxy) pentanoic acid amide;
N-(3-pyridyl)-3-thia-5-(4-methoxyphenoxy)-pentanoic acid amide:
N-(3-pyridyl)-3-thia-5-(3 4,5-trimethoxyphenoxy) pentanoic acid amide;
N-(3-pyridyl)methyl-3-thia-4-/4-(2-methoxyphenoxy)-methyl-(Z,E)-(1,3)-dioxolan-Z-yl/-butanoic acid amide;
N-(3-pyridyl)methyl-3-thia-4-/4-(4-methoxyphenoxy) methyl-(Z,E)-(1,3)-dioxolan-2-yl/-butanoic acid amide;
N-(3-pyridyl)methyl-3-thia-4-/2-(2-methoxyphenoxy)-methyl-(Z,E)-(1,3)-dioxolan-4-yl/-butanoic acid;
N-(3-pyridyl)methyl-3-thia-4-/4-(2-methoxyphenoxy) methyl-(Z,E)-(l,3)-dioxolan-4-yl/-butanoic acid amide;
N-(3-pyridyl)methyl-3-oxa-4-/4-(2-methoxyphenoxy methyl-(Z,E)-(1,3)-dioxolan-2-yl/butanoic acid amide.

The compounds of the invention of formula I are prepared by a process in which a compound of general formula II

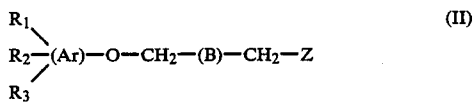

is reacted with a compound of general formula III

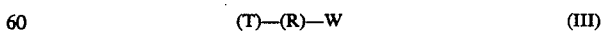

wherein R, $R_1$, $R_2$, $R_3$, Ar, B, T, are as above defined and one of Z and W is OH or —SH while the other is selected from the group of halogen, thioacetate, acetate, mesylate or tosylate. The reaction between a compound of formula II and a compound of formula III is carried out reacting stoichiometrical amounts of these reagents in a suitable solvent in presence of a stoichiometrical amount or a slight excess of a base. Suitable bases are alkaline or alkaline earth metals hydroxides, carbonates or alcoholates. Suitable solvents are methanol, ethanol, isopropanol, tert-butanol, water or their mixtures.

Suitable bases can also be sodium or potassium hydrides in an inert solvent, such as hydrocarbon, e.g. benzene, toluene, xylene, isooctane; an ether such as diethyl ether, diisopropyl ether, tert-butyl-ether, tetrahydrofuran, dioxane, dimethoxyethane or diglyme; dimethylformamide or dimethylsulphoxide.

The reaction is carried out at a temperature ranging from −20° C. to the solvent's reflux temperature, or anyway, at temperatures not exceeding 100° C. and the reaction time may range from one hour to some days. When in the compounds of formulae II and III one of W and Z is a free thiol group the reaction is carried out at room temperature in the presence of a slight molar excess of sodium ethoxide, preferably in ethanol, and usually it is complete in 2 hours. When in the compounds of formulae II and III one of W and Z is OH, the reaction is preferably carried out at room temperature in an inert solvent, such as, for instance, dimethylformamide, in the presence of a slight molar excess of an alkaline hydride such as, for instance, sodium hydride and it is complete in 3 hours.

Herebelow, for the sake of shortness, symbols used Previously for general formulae will have the same meaning, unless otherwise indicated in the context.

Compounds of general formula II can be prepared following known methods. Particularly, the preparation of compounds II wherein B is

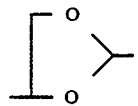

is summarized in the following scheme 1 dimethyl- or diethylacetale of a α-halogen aldehyde in the absence of a solvent, at a temperature ranging from 50° C. to 150° C., in presence or not of catalytic amounts of p-toluensulphonic or sulphosalicylic acid ranging from 10% molar to 25% molar with respect to the diol, or of a ion-exchange resin in acid form.

The reaction is carried out under a nitrogen atmosphere by heating a mixture of diol V with the suitable α-halo- aldehyde acetale (in a molar excess from 10% to 150%) removing by distillation the formed alcohol. Preferably 20% molar excess of α-chloro or α-bromo acetaldehyde dimethyl ( or diethyl-) acetale, 10% molar excess of p-toluensulphonic acid is reacted with the diol of formula V, at a temperature of 80° C., distilling off methanol or ethanol.

The compounds VI wherein Z' is iodine can be easily obtained by treatment of a compound of formula VI wherein Z' is Cl, Br with an excess of potassium iodide according to known methods.

The transformation of a compound of formula VI in a compound of formula VII wherein Z" is $CH_3COS-$ or $CH_3COO-$ is carried out by treatment of a compound of formula VI with an alkali acetate or thioacetate (in a molar excess from 100% to 300%). The reaction is carried out in an inert solvent such as dimethylsulphoxide, dimethylformamide, dimethylacetamide, hexamethylphosphotriamide, acetone, acetonitrile or water or their mixtures keeping the temperature in the range from 0° C. to 100° C., for a time from 1 hour to several days.

The halogen-acetate exchange is preferably carried out in dimethylsulphoxide, at 70° C., with potassium acetate, in a 100% molar excess, and the reaction is completed after 3 hours. The halogeno-thioacetate exchange preferably is carried out in acetone, for instance, potassium thioacetate (300% excess) at room temperature, the reaction being usually complete after a night.

The compounds of general formula VIII wherein Z''' is OH or SH may be prepared, if desired, by hydrolysis

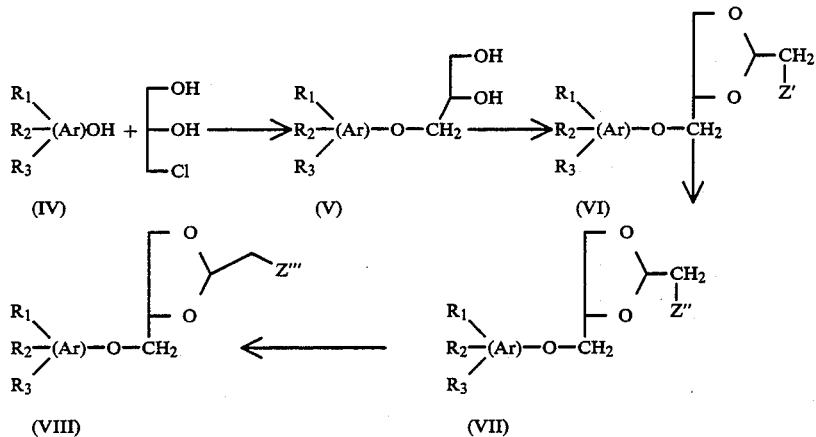

wherein Z' is Cl, Br and Z" is $OCOCH_3$ or $S-COCH_3$ and Z''' is OH or SH.

The compounds IV, that are commercially available or preparable according to known methods, are reacted with a 10% molar excess of a 3-halo-1,2-propandiol in the presence of a base such as potassium or sodium hydroxide in water or sodium ethoxide in ethanol, according to J. Org. Chem. (1950) 4986, for the preparation of diols of general formula V.

The compounds of general formula VI wherein Z' is halogen, are prepared by reacting compounds V with a of the corresponding acetates and thioacetates with aqueous concentrated solutions of ammonium hydroxide, in a water-miscible solvent such as dimethoxyethane, diglyme, triglyme, DMSO, THF, DMF, or their mixtures at room temperature in an inert gas atmosphere; the reaction time may range from a few minutes to some days. Preferred solvent is dimethoxymethane;

the reaction has been usually completed after 3 hours, at room temperature and under inert gas atmosphere.

The compounds of general formula I wherein B is a

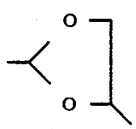

can be obtained in accordance with scheme 2

The aldehydes of general formula IX can be reduced, if desired, by sodium borohydride, to the corresponding alcohols XIII, according to known techniques.

The compounds XIII can then be transformed into the corresponding tosylates or mesylates of formula XIVa by reaction with a mesyl or tosyl chloride in the presence of a tertiary amine such as triethylamine or pyridine. Said reactions are well known in chemical literature. Alternatively, alcohols XIII can be transformed into the corresponding halides XIVc wherein Z' is chlorine or bromine by treatment respectively with

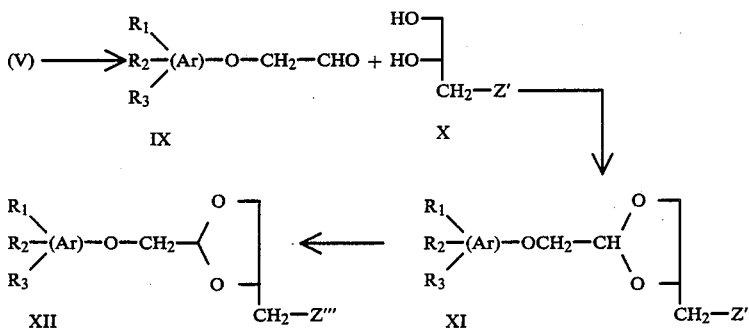

Oxidation with sodium periodate, in accordance with "Il Farmaco" Ed. Sc. 9, 156, (1956) of the diols V gives the aldehyde IX which can then be reacted with commercially available 3-halo-1,2-propane diols X to give the dioxolanes XI.

The reaction of compounds X, wherein Z' is Cl or Br, with compounds IX (dioxolane XI formation) can be carried out by heating to the reflux temperature a mixture of the aldehyde IX with a molar excess (from 10% to 50%) of the diol X , in an inert solvent such as benzene, toluene or xylene in presence of an acid catalyst, such as p-toluenesulphonic acid, sulphosalicylic acid or an ion-exchange resin in acid form by azeotropical removal of water in a time ranging from 1 to 12 hours. The following transformation of a compound of formula XI (Z'32 Cl or Br) in a compound of formula XII (Z'''=OH and SH) is performed according to the above discussed procedure illustrating the conversion of a compound of formula VI in a compound of formula VIII.

The preparation of compounds of formula I wherein B is a single bond is summarized in scheme 3 thionyl chloride or with CBr$_4$-tripheny lphosphine in accordance with Synth. Comm. (1986)16, 1926.

As above mentioned for the preparation of compounds VIII, the compounds XIVb wherein $Z^V$ is SCOCH$_3$ can be obtained by reacting both compounds XIVc and XIVa with potassium thioacetate. Thiols XIVb, wherein $Z^V$ is SH, can then be obtained by subsequent treatment with ammonium hydroxide in an inert solvent such as water-miscible ethers.

The preparation of compounds I wherein B is

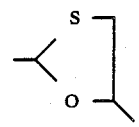

is summarized in the following scheme 4

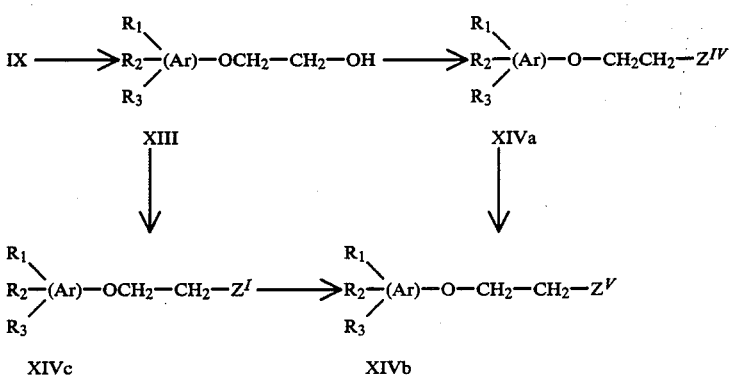

wherein $Z^{IV}$ is tosylate or mesylate, Z' is Br or Cl and $Z^V$ is SCOCH$_3$ or SH.

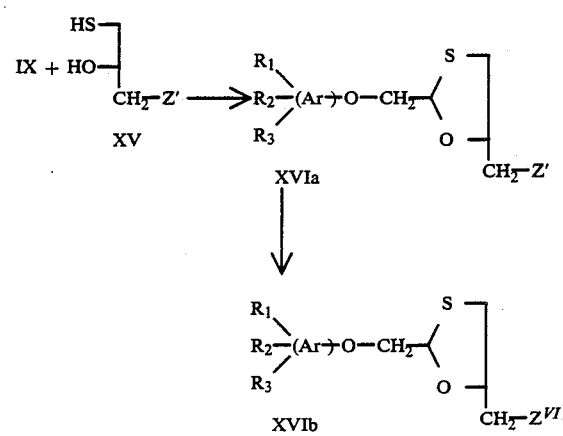

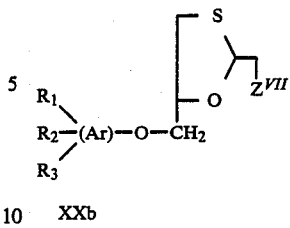

XXb using known procedures; monotosylates XVII are obtained by selective monotosylation of the primary hydroxy group of the diol V and are reacted with a 1:1 molar ratio of potassium thioacetate and tetrabutyl ammonium bromide (in a 300% molar excess in respect of the compounds XVII), at room temperature in an inert solvent such as acetonitrile or acetone to give compounds XVIII which are then transformed into thiols XIX by ammonolysis. Subsequent treatment of XIX with α-halo-acetaldehyde acetales affords the 1,3-thioxolanes XXa, wherein Z, is Cl or Br, whose halogen atom is transformed to give alcohols, acetates, thiols, thioacetates, mesylates or p-toluensulphonates of formula XXb, wherein $Z^{VII}$ is $OCOCH_3$, $CH_3SO_3-$, $CH_3-C_6H_4-SO_3-$, $-OH-SCOCH_3$, SH, using the procedure above described in the case of preparation of dioxolanes VII and VIII.

The reaction between compounds IX and the commercially available mercaptoalcohols XV, wherein Z' is Cl or Br, is carried out using reaction conditions similar to those above described in the reaction of compounds IX with diols X. 1,3-oxathiolanes XVIa, wherein Z' is Cl or Br, can then be transformed into the corresponding acetates, thioacetates, alcohols and thiols XVIb, wherein $Z^{VI}$ is $OCOCH_3$, $SCOCH_3$, OH or SH, according to the procedures above described in the dioxolanes XI series.

The compounds of general formula I wherein B is

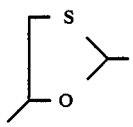

can also be prepared according to scheme 5

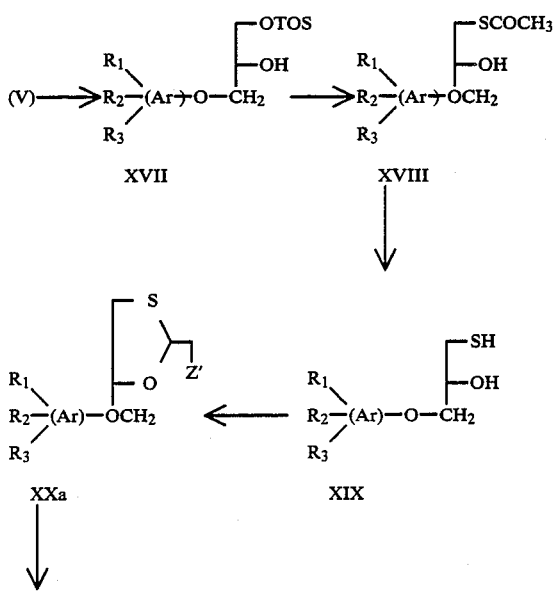

To improve yields and to minimize consumption of basic reagents, the acetylation of the phenolic group, when one of $R_1$, $R_2$ or $R_3$ is hydroxy may be carried out, if desired, using known procedures, by treatment with acetyl chloride, then removing the acetate protecting group by mild hydrolysis with aqueous or ethanol solutions of sodium or potassium hydroxides.

The compounds of formula III are commercially available or known substances that are prepared using known methods. So, for example, the compounds of formula III wherein T is 3-pyridyl, R is $CH_2$ and W is chlorine can be obtained by treating (3-pyridyl)methanol with $SOCl_2$; otherwise this latter compound may be reacted with mesyl chloride and then with potassium thioacetate to give compounds of formula III wherein T is 3-pyridyl, R is $CH_2$ and W is thioacetate and/or thiol after ammonolysis.

The transformation of compounds of formula III wherein W is Cl, Br or I into the corresponding alcohols or thiols can be carried out using the procedures for the Preparation of the compounds of general formula II.

The compounds of the general formula I wherein T is an ester or amide group may be obtained starting from a compound of formula I wherein T is COOH by reaction with a suitable alcohol or amine using procedures well known in the art.

The compounds of the invention of general formula I are therapeutically useful substances, devoid of toxic effects and conveniently used as bronchodilator, mucus-regulating and antitussive agents. When administered by oral and intraperitoneal route to mice and rats (male and female) they are devoid of acute toxic effects; $LD_{50}$ ranging from 1 to 5 g/Kg are measured.

The compounds of the invention are particularly useful as antitussive, fluidifying of bronchial secretions and antiinflammatory agents.

The ability of a drug to modify the tracheo-bronchial mucus secretion is evaluated measuring the excretion of a dyestuff in the respiratory tree.

According to the procedure of M. Mawatari, Kagoshima Daigaken Igaken Zasshi, 27, 561 (1976), Albino Swiss female mice are treated by oral route with the drug and, 5 minutes after, with a 0.5 aqueous uranine solution (0.1 ml/10 g body weight) by subcutaneous route. The animals are sacrified 30 minutes after; the respiratory tree is excised and accurately washed. The washing fluids (BAL) are collected and evaluated for the uranine content using a spectrofluorimetric technique.

Therapeutically active drugs such as bromexine and sobrerol are known to increase the uranine content in the BAL's in a dose dependent way in respect to the control values (BAL's of animal treated with vehicle). Red phenol is also used as dyestuff; according to the method of H. Hengler et al., (J. Pharm. Meth., 11, 151, 1984) the dyestuff is administered as a 5% aqueous suspension intraperitoneally (500 mg/kg) 30 minutes after oral treatment with the drug (or placebo). Albino Swiss male mice are used in this test and the animals are killed 30 minutes after dye treatment. The dye content in BAL's is evaluated spectrometrically at 546 nm.

An increased red phenol secretion in BAL's after drug treatment means stimulation of mucus production.

In the following table, the pharmacological results, obtained with representative examples of the compounds of the invention:
3-thia-5-(2-methoxy-phenoxy)-pentanoic acid (substance A);
N-(3-pyridyl)methy 1-3-thia-5 (2-methoxy-phenoxy)-pentanoic acid amide (substance B);
3-thia-4-[4-(2-methoxy-phenoxy)methyl-(Z,E)-dioxolan-2-yl]-butanoic acid (substance C);
N-(3-pyridyl)methyl-3-thia-4-[4-(2-methoxy-phenoxy)-methyl-(Z,E)-(1,3)-dioxolan-2-yl]-butanoic acid amide substance D)
are reported and compared with those obtained with the above cited reference substances:bromexine (substance E) and sobrerol (substance F).

| | % INCREASE OF DYESTUFF SECRETION IN BAL (vs. untreated animals) | | | | | | | | | | |
| SUBSTANCE | RED PHENOL | | | | | | URANINE | | | | |
| mg/kg os | A | B | C | D | E | F | A | B | C | D | E | F |
|---|---|---|---|---|---|---|---|---|---|---|---|---|
| 25 | 25 | 12 | 47 | 49 | 28 | nt | 45 | 70 | 25 | 66 | 0 | nt |
| 50 | 50 | 73 | 83 | 120 | 69 | 48 | 98 | 140 | 52 | 132 | 50 | 54 |
| 100 | 104 | 126 | 143 | 179 | 83 | 69 | 138 | 190 | 101 | 284 | 63 | 104 |
| 200 | nt | nt | nt | nt | nt | 111 | nt | nt | nt | nt | nt | 144 | nt = not tested
E,F: reference substances

The red phenol test is also useful for evaluating long-lasting action of the investigated drugs. Infact, a substance can be administered 2, 1 and ½ hours before the intraperitoneal administration of the red phenol marker. If the animals are killed, as usual, half an hour after the dyestuff treatment, the overall time of drug action increases from 1 hr to 1½ and 2½ hrs respectively.

The results of this study, wherein full active fixed doses were used, are reported in the following table.

| | | TIME-COURSE OF % INCREASE OF RED PHENOL EXCRETION (vs. untreated animals) | | |
| | | | overall experiment hours | |
| SUBSTANCE | mg/kg (os) | 1 | 1½ | 2½ |
|---|---|---|---|---|
| A | 100 | 104 | 98 | 62 |
| B | 100 | 126 | 119 | 62 |
| C | 100 | 143 | 72 | 42 |
| D | 100 | 179 | 111 | 58 |
| REFERENCE SUBSTANCES | | | | |
| E | 100 | 98 | 61 | 21 |
| F | 200 | 108 | 73 | 30 |

The above mentioned compounds of the invention (substances A–D) have been also tested as antitussive drugs. All the compounds possess a good activity; after oral administration (50 mg/kg) a 50% inhibition of cough (induced by aerosol of a 30% aqueous solution of citric acid) is measured.

They are useful for treatment of bronchial hyperreactivity that is thought to be partially a consequence of inflammatory conditions in the broncho-trachealrespiratory tree.

Infiltration of eosinophiles, desquamation of wide areas of epithelium, mucus hypersecretion and bronchial smooth muscle hyperplasia are aspects of these inflammatory events. In animal models, the compounds of the invention are particularly able to prevent many of these experimentally induced events.

For example, the substance B (after e.v. treatment to anaesthetized guinea-pigs submitted to a forced tobacco-smoking respiration, in the range of dosages from 5 to 30 mg/kg) is able to reduce the hyperreactive spasmus induced by acetylcholine challenge in dose dependent way. Positive reference substances in this novel experimental procedure are for example 6-α-methylprednisolone and sodium dichromoglicate (i.m. administration).

For the above mentioned therapeutical uses, the compounds of the invention are formulated in pharmaceutical compositions, using conventional techniques and eccipients, as described in "Remington's Pharmaceutical Sciences' Handbook", Hack Publ. Co., New York, U.S.A. Examples of said compositions include capsules, tablets, packets, syrups, drinkable solutions, suppositories, vials for parenteral or inhalatory administration, controlled-release forms, etc.

Dosages will range from 100 and 2000 mg pro day as total amount and will be administered in divided portions during the day, the specified dosage varying depending on the age, weight and conditions of the patient, as well as on the administration route; higher dosages even for long periods have no contraindications.

The invention will be illustrated by the following non-limiting examples.

EXAMPLE 1

A solution of 4-methoxyphenol (20 g) in absolute ethanol is slowly added at room temperature to a solution of sodium ethoxide in ethanol (160 ml) prepared "in situ" dissolving 4.2 g of sodium under nitrogen atmosphere.

After 30′ a solution of 3-chloro-propane-1,2-diol (14.7 ml) in absolute ethanol (20 ml) is added and the resulting solution is refluxed for 4 hours. After cooling and removal of salts by filtration, the mixture is dried in vacuum and the residue is crystallized from diethylether. 29.8 g of 3-(4-methoxy)phenoxy-propane-1.2-diol, m.p. 67°–69° C., are obtained.

EXAMPLE 2

Using a suitable phenol in the procedure of example 1, by reaction with 3-chloro-propane-1,2-diol the following propane-1,2-diols are obtained:
3(2-hydroxy-phenoxy)-propane-1,2-diol;
3(3-4-5-trimethoxy-phenoxy)-propane-1,2-diol;
3(3-5-dimethoxy-4-hydroxy-phenoxy)-propane-1,2-diol;
3(3,5-ditert.butyl-4-hydroxy-phenoxy)-propane-1,2-diol;
¾(imidazol-1-yl)-phenoxy/-propane-1,2-diol;
3(4-acetamido-phenoxy)propane-1,2-diol;
3/2-methoxy-4-allyl-phenoxy/-propane-1,2-diol.

EXAMPLE 3

3-(4-methoxy-phenoxy)-propane-1,2-diol (65.3 g) is added to a solution of sodium periodate (60.5 g) in water (600 ml), cooled at 0°, and the resulting suspension has been stirred at 0° C. for two hours. After addition of ethyl acetate ( 1l) the organic phase is separated, washed with water, dried on sodium sulphate. Removal of the solvent under vacuum affords 2(4-methoxy-phenoxy)ethanale (45 g) as a clear oil.
IR: $\gamma 1725$ cm$^{-1}$ ($\gamma$=CO); 835 cm$^{-1}$ ($\delta$CH are OUT, adjacent 2H); NMR (CDCl$_3$) $\delta$=3,8 3H (s) OCH$_3$; $\delta$=4,5 2H (s) —CH$_2$—CHO—; $\delta$=9,8, 1H (s) CHO.

EXAMPLE 4

Using a suitable 3-substituted-propane-1,2-diol of the example 2 in the procedure of example 3, the following 2-substituted ethanales are obtained:
2(2-methoxyphenoxy)ethanale (m.p. 65°–67° C.);
2(3,4,5-trimethoxyphenoxy)ethanale;
2/4-(imidazol-1-yl)phenoxy/-ethanale;
2-/2-methoxy-4-allyl-phenoxy/-ethanale.

EXAMPLE 5

Sodium borohydride (3.78 g) is added to a solution of 2(2-methoxyphenoxy)ethanale (16.6 g) in methanol (20 ml) cooled at 0° C., in small portions, keeping the temperature under 10° C. After 30′ at 10° C. the reaction mixture is poured in aqueous NaH$_2$PO$_4$ 30% (200 ml) and extracted with ethyl acetate ( 3×100 ml). The organic extracts are washed with water, dried on Na$_2$SO$_4$ and concent rated under vacuum to give 2-(2-methoxy)-ethanol (13.5 g) as a yellow oil (NMR (CDCl$_3$)=2,8,3,7, 1H (m) OH disappears with D$_2$O;
IR:=3000–3600 cm$^{-1}$ (OH). A solution of 5 g of the above product in dichlooroethane (40 ml), cooled at 0° C., is treated with triethylamine (4.6 ml) and with a solution of methanesulphonyl chloride (2.55 ml) in dichloroethane which is then added dropwise. The reaction mixture is stirred for 3 hours at room temperature and then filtered.

The filtrate is washed with water, 5% aqueous NaHCO$_3$ and again with water. After anhydrification on sodium sulphate and removal of the solvent under vacuum the residue is crystallized from isopropyl ether to give 5.4 g of 2-(2-methoxyphenoxy)-ethyl methanesulphonate, m.p. 73°–76° C.

EXAMPLE 6

After reduction of a suitable 2-substituted ethanale of the examples 3 and 4 with NaBH$_4$ and after reaction with methane sulphonyl chloride, according to example 5, the following methanesulphonates are obtained:
2-/2-methoxy-4-allyl-phenoxy /-ethyl methanesulphonate;
2(4-methoxyphenoxy)ethyl methanesulphonate;
2-(4-imidazol-1-yl-phenoxy)ethyl methanesulphonate;
2-(4-acetamidophenoxy)ethyl methanesulphonate.

EXAMPLE 7

A solution of 3-(2-methoxy-phenoxy)-propane-1,2-diol (4.7 g) in pyridine, cooled at 5°–10° C., is treated under stirring with a solution of p-toluensulphonylchloride (4.5 g) in benzene (70 ml). The reaction mixture is stirred overnight at room temperature, then it is washed with 2N HCl (3×100 ml) and with water, dried on Na$_2$SO$_4$ and evaporated to dryness in vacuum. The oily residue is purified by column chromatography (silica gel—230-400 mesh hexane/AcOEt=3/1) to yield 5 g of 3-(2-methoxy-phenoxy)-2-hydroxy-1-propyl. p-toluensulphonate. (oil. NMR (—CDCl$_3$): $\delta$=2,4 3H (s) CH$_3$SO$_2$; $\delta$=3.75–4.4 5H (m) OCH$_3$+OCH$_2$.

Potassium thioacetate (2 g) and tetrabutylammonium bromide (0.7 g) are added to a solution of 4 g of this compound in acetonitrile (50 ml) and the mixture is refluxed for 3 hours. After evaporation to dryness, the residue is partitioned between water and ethyl acetate and the organic phase is evaporated to dryness. A solution of the residual oil (2.5 g of 3(2-methoxyphenoxy)-1-acetylmercapto-(propane-2-ol) in dimethoxyethane (50 ml) is treated with 28% aqueous ammonium hydroxide (10 ml); the mixture is kept for 3 hours at room temperature and then it is evaporated under vacuum. The oily residue is purified by column chromatography (silica gel—230-400 mesh—AcOEt) to give 1.7 g of 3-(2-methoxy-phenoxy)-1-mercapto-propan-2-ol.

EXAMPLE 8

Using in the procedure of example 7 a suitable 3-(aryloxysubstituted)-1,2-propane-diol of examples and 2, the following compounds are obtained:
3(4-methoxy-phenoxy)-1-mercapto-propane-2-ol;
3(3,4,5-trimethoxy-phenoxy)-1-mercapto-propane-2-ol;
3/4-(imidazol-1-yl)phenoxy/-1-mercapto-propane-2-ol;
3(4-acetamido-phenoxy)-1-mercapto-propane-2-ol.

EXAMPLE 9

A stirred mixture of 3-(2-methoxy-phenoxy)-propane-1,2-diol (100 g), sulphosalicylic acid (3 g) and 2-bromo-ethanaldiethylacetal is heated for 4 hours at 100° C., distilling off ethanol. After cooling, the reaction mixture is diluted with ethyl acetate (100 ml), washed with 5% aqueous NaHCO$_3$ and water; after drying on Na$_2$SO$_4$ the solvent is evaporated in vacuum. The residue is crystallized from diisopropyl ether to afford 15.4 g of (Z,E)-2-bromomethyl-(2-ethoxy-phenoxy)methyl-(1,3)-dioxolane, m.p. 45°-53° C. A solution of this compound (10 g) in CCl4 (25 ml) is adsorbed on a silica gel column (400 g) and eluted with AcOEt/petroleum ether (1:1) to give 4 g of (E)-2-bromomethyl-4-(2-methoxy-phenoxy)-methyl-1,3-dioxolane, m.p. 52°-53° C. and 4 g of (Z)-2-bromomethyl-4-(2-methoxy-phenoxy)-methyl-1,3-dioxolane, m.p. 60°-61° C. (after crystallization from EtOH).

EXAMPLE 10

Using in the procedure of example 9 a suitable 3-substituted-1,2-propandiol, the following compounds are obtained:
(Z,E)-4-(2-hydroxy-phenoxy)methyl-2-bromomethyl-(1,3)-dioxolane;
(Z,E)-4-(3,4,5-trimethoxyphenoxy)methyl-2-bromomethyl-(1,3)-dioxolane;
(Z,E)-4-(3,5-dimethoxy-4-hydroxy-phenoxy)methyl-2-bromomethyl-(1,3)-dioxolane;
(Z,E)-4-(3,5-ditert.butyl-4-hydroxy-phenoxy)-methyl-2- bromomethyl-(1,3)-dioxolane;
(Z,E)-4-/4-(imidazol-1-yl)phenoxy/-methyl-2-bromomethyl(1,3)-dioxolane;
(Z,E)-4-(4-acetamidophenoxy)methyl-2-bromomethyl-(1,3)-dioxolane;
(Z,E)-4-/2-methoxy-4-allyl-phenoxy/-methyl-2-bromomethyl-(1,3)-dioxolane;
(Z,E)-4-(4-methoxyphenoxy)methyl-2-bromomethyl (1,3)-dioxolane.

EXAMPLE 11

A stirred suspension of potassium acetate (13.5 g) and of (Z,E)-2-bromomethyl-4-(4-methoxy-phenoxy)-methyl-1,3-dioxolane (20 g) in dimethylsulphoxide (100 ml) is heated for 2 hours at 100° C. After cooling the reaction mixture is poured in iced water (250 ml) and extracted with diethylether. After anidrification on Na2SO4 and solvent removal, the purification of the crude residue by column chromatography (silica gel 30-100 mesh, eluent: hexane/AcOEt=3:1) yields 15 g of (Z,E)-2-acetoxymethyl-4-(4-methoxyphenoxy)-methyl-(1,3)-dioxolane as a clear oil.

IR=1735 cm$^{-1}$ ($\gamma$ C=O), $\gamma$=1240 cm$^{-1}$ (C—O as,sim) $\gamma$=1100 cm$^{-1}$ ($\gamma$ as C—O—C alicyclic ethers); NMR (CDCl3): $\delta$=2.34 3H (s) CH3CO.

A solution of this compound in dimethylsulhpoxide is treated with a solution of potassium carbonate (17 g) in water (60 ml) and heated for 3 hours at 50° C. The aqueous solution is saturated with NaCl and extracted with ethyl acetate. The extracts are dried, decolourized with charcoal and evaporated to dryness under vacuum to give after trituration with diisopropylether 12 g of (Z,E)-2-hydroxymethyl-4-(4-methoxyphenoxy)methyl-1,3-dioxolane, m.p. 44°-49° C.

EXAMPLE 12

A suitable 4-substituted-2-halomethyl-(1,3)-dioxolane of examples 9 and 10 is reacted according to the example 11 and the following compounds are obtained:
(E)-4-(2-methoxyphenoxy)methyl-2-hydroxymethyl-(1,3)-dioxolane, m.p. 68°-69° C.;
(Z)-4-(2-methoxyphenoxy)methyl-2-hydroxymethyl (1,3)-dioxolane, m.p. 57°-59° C.;
(Z,E)-4-(4-methoxyphenoxy)methyl-2-hydroxymethyl (1,3)-dioxolane;
(Z,E)-4-(3,4,5-trimethoxyphenoxy)methyl-2-hydroxymethyl-(1,3)-dioxolane;
(Z,E)-4-(3,5-dimethoxy-4-hydroxy-phenoxy)methyl-2-hydroxymethyl-(1,3)-dioxolane;
(Z,E)-3-(3,5-ditert.butyl-4-hydroxy-phenoxy)methyl-2-hydroxymethyl-(1,3)-dioxolane;
(Z,E)-4-(4-acetamidophenoxy)methyl-2-hydroxymethyl (1,3)-dioxolane;
(Z,E)-4-/(imidazol-1-yl)phenoxy/methyl-2-hydroxymethyl-(1,3)-dioxolane;
(Z,E)-3-/2-methoxy-4-allyl-phenoxy/-methyl (1,3)-dioxolane.

EXAMPLE 13

A stirred suspension of (Z,E)-2-(2-methoxyphenoxy)-methyl-4-bromomethyl-1,3-dioxolane (6.84 g) and potassium thioacetate (6.08 g) in acetonitrile (300 ml) is refluxed for 5 hours under inert gas atmosphere.

The solvent is concentrated to a small volume and the residual mixture is poured into iced water.

The aqueous phase is extracted with ethyl aceate to give after the usual work-up an oily residue which is purified by column chromatography (silica gel—230-400 mesh—hexane/ethyl acetate=1:1) so yielding 3 g of (Z,E)-2-(2-methoxyphenoxy)-methyl-4-acetylthiomethyl(1,3)-dioxolane as a limpid oil, (IR=$\gamma$ 1690 cm$^{-1}$ (C=O of RCOSR) NMR (CDCl3): $\delta$=2.3 3H (s) CH3—COS—; $\delta$=3.1-2.9 2H (d) CH2—S—; $\delta$=5.2 1H (t)—O—CH—O—).

A solution of 2 g of this compound in dimethoxyethane (15 ml) is treated with concentrated ammonium hydroxide (5 ml) at room temperature, under nitrogen. After 24 hours the reaction mixture is concentrated to dryness under vacuum and the residue is diluted with ethyl acetate. The organic phase is washed with water (2×5 ml), dried on Na2SO4 and concentrated to dryness. The residue is purified by column chromatography (silica gel—230-400 mesh—hexane/ethyl acetate=1:2) and 0.7 g of 2-(Z,E)-2-methoxyphenoxy)-methyl-4-mercaptomethyl-(1,3)-dioxolane are obtained as uncoloured oil (IR=$\gamma$ 2250 cm$^{-1}$, (SH) NMR (CDCl3) $\delta$=3-3.15 2H dd—CHS—.

EXAMPLE 14

Using in the procedure of example 12 a suitable 2-halo-methyl-dioxolane of the examples 9 and 10, the following compounds are obtained:
(Z,E)-2-acetylthiomethyl-4-(4-methoxy-phenoxy) methyl-(1,3)-dioxolane;
(Z,E)-2-mercaptomethyl-4-(4-methoxy-phenoxy)-methyl (1,3)-dioxolane;
(Z,E)-2-acetylthiomethyl-4-(3,4,5-trimethoxyphenoxy) methyl-(1,3)-dioxolane.

EXAMPLE 15

A solution of (E)-2-hydroxymethyl-4-(2-methoxyphenoxy) methyl-1,3-dioxolane in dimethylformamide (DMF) is added under nitrogen atmosphere to a suspension of sodium hydride (80% in mineral oil, 0.57 g). The mixture is warmed at 40° C. for 30', and then cooled at 0°-10° C., slowly added dropwise thereto a solution of ethyl bromoacetate (2.12 ml) in DMF. After 12 hours at room temperature, the reaction mixture is diluted with aqueous NaH2PO4 (100 ml) and extracted with ethyl acetate. After washing with water (3×30 ml) the organic phase is dried on Na2SO4 and evaporated under vacuum to give 2.7 g of ethyl 4-/(E)-4-(2-methoxyphenoxy)methyl-(1,3)-dioxolane-2-yl/-3-oxa-butanoate as a clear oil (NMR CDCl₃):

δ=1,2,3H (t) CH₃ —CH₂—O; δ=3,6, 2H (d)—CH₂—O—CH₂COOEt, δ=3,8, 3H (s) CH₃—O—, δ=6,8 4H (s) CH aromatic).

A suspension of this compound in aqueous NaOH N (20 ml) is stirred for 3 hours at room temperature to obtain a clear solution which is then extracted with ethyl acetate (2×10 ml) and the organic phase is discarded. The aqueous phase is acidified to pH 2.5-3 by treatment with a 10% aqueous KHSO₄ solution and extracted with ethyl acetate (5×10 ml). These organic extracts are collected, washed with water (2×10 ml) dried on Na₂SO₄ and concentrated to dryness under vacuum. The residue crystallizes from diisopropyl ether affording 2.0 g of 3-oxa-4-/4-(2-methoxy-phenoxy)-methyl-(E) (1,3)-dioxolane-2-yl/butanoic acid; m.p.86°-88° C.

In a similar way and starting from (Z)-4-/(2-methoxy-phenoxy)-methyl/-2-bromo-methyl (1,3)-dioxolane and from a (1:1) mixture of the Z and E isomers, the following compounds are obtained respectively:

3-oxa-4-/4-(2-methoxyphenoxy)methyl-(Z)-(1,3) dioxolan-2-yl/butanoic acid, m.p. 64°-66° C. and
3-oxa-4-/(2-methoxyphenoxy)methyl-(Z,E)-(1,3)-dioxolan-2-yl/butanoic acid, m.p. 68°-69° C.

EXAMPLE 16

Using in the procedure of example 14 a suitable 4-substituted-2-bromomethyl-dioxolane of the examples 9 and 10, the following compounds are obtained:
3-oxa-4-(3,5-ditert.butyl-4-hydroxyphenoxy)methyl (Z,E)-(1,3)-dioxolan-2-yl/-butanoic acid;
3-oxa-4-/4-(3,5-dimethoxy-4-hydroxyphenoxy)methyl (Z,E)-(1,3)-dioxolan-2-yl/-butanoic acid;
3-oxa-4-/4-(3.4,5-trimethoxyphenoxy)methyl (Z,E)-(1,3)-dioxolan-2-yl/-butanoic acid;
3-oxa-4/4-(2-methoxy-4-allyl-phenoxy)methyl-(Z,E)(1,3)-dioxolan-2-yl/butanoic acid;
3-oxa-4-/4-(4-methoxy-phenoxy)methyl-(Z,E)-(1,3) dioxolan-2-yl/-butanoic acid.

EXAMPLE 17

A solution of methyl thioglycolate (1.62 ml) in methanol (5 ml) is added dropwise under an inert gas atmosphere to a stirred solution of sodium methoxide (from 0.46 g of Na) in methanol (40 ml); after 30 minutes 5 g of (Z,E)-2-brono-methyl-4-(2-methoxyphenoxy)methyl-1,3-dioxolane are added dropwise to the mixture.

The mixture is refluxed for 2 hours, diluted with aqueous 2N NaOH (8.5 ml) and heated again for 2 hours at the reflux temperature.

After concentration to a small volume the mixture is diluted with water (20 ml) and washed with ethyl acetate and these extracts are discarded. The aqueous phase is then acidified to pH 2.5 (H₂SO₄2N) and extracted with ethyl acetate (3×20 ml). The combined extracts are dried on Na₂SO₄, evaporated to dryness under vacuum to yield 3.2 g of 3-thia-4-/4-(2-methoxy-phenoxy)-methyl-(Z,E)-(1,3)-dioxolan-2-yl/-butanoic acid (m.p. 62°-67° C.). Using in the same procedure, pure (Z) or (E)-2-bromomethyl-dioxolanes the following pure geometrical isomers 3-thia-4-/4-(2-methoxyphenoxy)methyl-(Z)-(1,3)- dioxolan-2-yl/butanoic acid (m.p. 82°84° C.) and 3-thia-4-/4-/2-methoxyphenoxy)methyl-(E)-(1,3-dioxolan-2-yl/-butanoic acid (m.p. 78°-82° C.), are obtained.

EXAMPLE 18

Using in the procedure of example 17 a suitable 4-substituted 2-halomethyl-dioxolane of the examples 9 and 10, the following compounds are obtained:
3-thia-4-/4-(4-methoxy-phenoxy)methyl-(Z,E)-(1,3)dioxolane-2-yl/butanoic acid;
3-thia-4-/4-(2-hydroxy-phenoxy)methyl-(Z,E)-(1,3) dioxolane-2-yl/-butanoic acid;
3-thia-4-/4-(3,4,5-trimethoxy-phenoxy)methyl-(Z,E) (1,3)-dioxolane-2-yl/-butanoic acid;
3-thia-4-/4-(3,5-dimethoxy-4-hydroxy-phenoxy)methyl (Z,E)-(1,3)-dioxolan-2-yl/butanoic acid;
3-thia-4-/4-(4-imidazol-1-yl-phenoxy)methyl-(Z,E) (1,3)-dioxolane-2-yl/-butanoic acid;
3-thia-4-/4-(3,5-ditert.butyl-4-hydroxy-phenoxy)methyl (Z,E)-(1,3)-dioxolane-2-yl/-butanoic acid;
3-thia-4-/4-(4-acetamido-phenoxy)methyl-(Z,E) (1,3)-dioxolane-2-yl/-butanoic acid;
3-thia-4-/4-(2-methoxy-4-allyl-phenoxy)methyl-(Z,E) (1,3)-dioxolane-2-yl/butanoic acid.

EXAMPLE 19

Using N-acetyl-L-cysteine methylester and 2-(S)-mercapto-propionylglycine ethylester instead of methylthioglycolate in the procedure of example 17 and by reaction with a suitable 2-halo-methyl-dioxolane of examples 9 and 10, the following compounds are obtained:
2-(acetylamino)-4-thia-5-/4-(2-methoxyphenoxy)methyl(Z,E)-(1,3)-dioxolane-2-yl/-pentanoic acid;
2-(acetylamino)-4-thia-5/4-(4-methoxy-phenoxy)-methyl-(Z,E)-(1,3)-dioxolane-2-yl/-pentanoic acid;
(2S)-2-methyl-3-thia-4-/4-(2-methoxy-phenoxy)methyl (Z,E)-(1,3)-dioxolane-2-yl/-butanoylglycine;
(2S)-2-methyl-3-thia-4-/4-(4-methoxy-phenoxy)methyl (Z,E)-(1,3)-dioxolan-2-yl/-butanoyl glycine.

EXAMPLE 20

Using in the procedure of example 9 a 3-substituted-propane-1-mercapto-2-ol of examples 7 and 8 instead of the 3-substituted propane-1,2-diol by reaction with 2-bromo-ethanol diethyl acetal in presence of sulfosalicylic acid, the following (1,3)-thioxolanes are obtained:
(Z,E)-4-(2-methoxy-phenoxy)methyl-2-bromomethyl-(1, 3)thioxolane;
(Z,E)-4-(4-methoxy-phenoxy)methyl-2-bromomethyl (1,3)-thioxolane;
(Z,E)-4-(3,4,5-trimethoxy-phenoxy)methyl-2-bromomethyl-(1,3)-thioxolane;
(Z,E)-4-(4-imidazol-1-yl-phenoxy)methyl-2-bromomethyl-(1,3)-thioxolane;
(Z,E)-4-(4-acetamido-phenoxy)methyl-2-bromomethyl (1,3)-thioxolane.

EXAMPLE 21

By reaction of a 2-halomethyl-(1,3)-thioxolane of example 20 with ethyl thioglycolate, N-acetylcysteine methylester or 2S-mercaptopriopionylglycine, according to the examples 17 and 19, the following compounds are obtained:
3-thia-4-/4-(2-methoxy-phenoxy)methyl-(Z,E)(1,3)-thioxolane-2-yl/-butanoic acid;
3-thia-4-/4-(4-methoxy-phenoxy)methyl-(1,3)-thioxolan-2-yl/-butanoic acid;
3-thia-4-/4-(3,4,5-trimethoxy-phenoxy)methyl-(Z,E)-(1,3)-thioxolan-2-yl/-butanoic acid;

3-thia-4-/4-(4-imidazol-1-yl-phenoxy)methyl-(Z,E)-
(1,3)-thioxolan-2-yl/-butanoic acid;
3-thia-4-/4-(4-acetamido-phenoxy)methyl-(Z,E)-(1,3)-
thioxolan-2-yl/-butanoic acid;
2-(acetylamino)-4-thia-5/4-(2-methoxy-phenoxy)-methyl-(Z,E)-(1,3)-thioxolan-2-yl/-pentanoic acid;
2-acetylamino-4-thia-5-/4-(4-methoxy-phenoxy)methyl (1,3)-thioxolan-2-yl/pentanoic acid;
(2S)-2-methyl-3-thia-4-/4-(2-methoxy-phenoxy)methyl (Z,E)-(1,3)-thioxolane-2-yl/-butanoyl-glycine.

EXAMPLE 22

A solution of 2-(2-methoxy-phenoxy)ethanale (48 g) 3-bromo-1,2-propandiol (52,7 g) and p-toluensulphonic acid (3.85 g) in benzene (500 ml) is refluxed for 5 hours with azeotropic removal of the water formed during the reaction.

Potassium carbonate (20 g) is added to the cooled solution, the suspension is stirred overnight, filtered and the filtrate is evaporated to dryness in vacuum to give an oily residue which is distilled in high vacuum (m.p. 178°–185° C. 0.5 mm Hg) to obtain 33.4 9 of (Z,E)-2-(2-methoxyphenoxy)-4-bromomethyl-1,3-dioxolane.

EXAMPLE 23

Using in the procedure of example 22 a suitable 2-substituted ethanale of examples 3 and 4, the following compounds are obtained:
(Z,E)-2-(4-methoxy-phenoxy)methyl-4-bromomethyl-(1,3)-dioxolane;
(Z,E)-2-(3,4,5-trimethoxyphenoxy)methyl-4-bromomethyl 1,3)-dioxolane;
(Z,E)-2-(4-imidazol-1-yl-phenoxy)methyl-4-bromomethyl (1,3)-dioxolane;
(Z,E)-2-(2-methoxy-4-allyl-phenoxy)-methyl-4-bromomethyl-(1,3)-dioxolane.

EXAMPLE 24

By reaction of a (Z,E)-2-(2-methoxy-phenoxy)-methyl-4-bromomethyl-1,3-dioxolane of examples 22 and 23 with potassium acetate, according to the example 11, or with potassium thioacetate, according to the example 13, or respectively with methyl thioglycolate or N-acetylcysteine methylester, according to the examples 17 and 19, the following compounds are obtained:
(Z,E)-2-(2-methoxy-phenoxy)methyl-4-acetoxymethyl-dioxolane;
(Z,E)-2-(2-methoxy-phenoxy)methyl-4-hydroxymethyldioxolane;
(Z,E)-2-(2-methoxy-phenoxy)methyl-4-acetylthiomethyl dioxolane;
(Z,E)-2-(2-methoxy-phenoxy)methyl-4-mercaptomethyl dioxolane;
3-thia-4-/2-(2-methoxy-phenoxy)methyl-(Z,E)-(1,3)-dioxolan-4-yl/-butanoic acid;
2-(acetylamino)-4-thia-5-/2-(2-methoxy-phenoxy)-methyl (Z,E)-(1,3)-dioxolan-4-yl/-pentanoic acid (m.p. 80°–82° C.).

EXAMPLE 25

By reaction of a methanesulphonate of examples 5 and 6 with a methyl thioglycolate, according to the example 17, the following compounds are obtained:
3-thia-5-(2-methoxy-phenoxy)-pentanoic acid, m.p. 69°–71° C.;
3-thia-5-(4-methoxy-phenoxy)pentanoic acid;
3-thia-5-(3,4,5-trimethoxy-phenoxy)pentanoic acid;
3-thia-5-(3,5-dimethoxy-4-hydroxy-phenoxy)pentanoic acid;
3-thia-5-(4-imidazol-1-yl-phenoxy)pentanoic acid;
3-thia-5-(4-acetamido-phenoxy)pentanoic acid;
3-thia-5-(2-methoxy-4-allyl-phenoxy)-pentanoic acid.

EXAMPLE 26

Methanesulphonylchloride (31.7 ml) is slowly added dropwise to a stirred solution of (3-pyridyl)-methanol (39.6 ml) and triethylamine (55.7 ml) in dichloroethane (600 ml), cooled at 0° C.

The reaction mixture is left for 40 minutes at 0° C. and filtered. The organic filtrate is washed with water (2×100 ml) and then it is treated with a solution of potassium thioacetate (48 g ) in water (250 ml) for 2 hours under vigorous stirring.

The separated organic phase is washed with water (2×100 ml), dried on $Na_2SO_4$ and evaporated to dryness in vacuum to give an oily residue of crude 3-(acetylthiomethyl)pyridine (48 g).

A solution of potassium carbonate (1.4 g) in water (5 ml) and 2-(2-methoxy-phenoxy)ethyl-methane sulphonate (1.05 g) are added to a solution of crude 3-(acetylthiomethyl)-pyridine (0.7 g) in ethanol (20 ml); the stirred mixture is heated for 2 hours at 50° C.

The mixture is cooled, diluted with water and extracted with ethyl acetate (2×20 ml). The collected organic extracts are washed with water (3×10 ml), dried and evaporated to dryness in vacuum. The oily residue is purified by column chromatography (silica gel—230—400 mesh—AcOEt) to give 1 g of 1-(3-pyridyl)-2-thia-4-(2-methoxy-phenoxy) butane as a clear oil.

NMR ($CDCl_3$): $\delta=2{,}75{,}2H$ (t) $CH_2$—S—; $\delta 3.8-3.85, 3+2H$ (2s)—$OCH_3$+S—$CH_{-Py}$; $\delta=4.15$ 2H (t) —$CH_2$—O—; $\delta=6.8$ 4H (s)phenyl; 7–8.7 4H (m)-pyridyl.

EXAMPLE 27

By reaction of a suitable halomethyl-(1,3)-dioxolane of examples 9, 10, 22 and 23 or of a suitable halomethyl-(1,3)-thioxolane of example 20 and/or suitable methanesulphonates of the examples 5 and 6 with a (acylthiomethyl)pyridine prepared according to example 26, the following compounds are obtained:
(Z,E)-2-(3-pyridyl-methylthio)methyl-4-(2-methoxy-phenoxy)-methyl-(1,3)-dioxolane;
(Z,E)-4-(3-pyridyl-methylthio)methyl-2-(2-methoxy-phenoxy)-methyl-(1,3)-dioxolane;
(Z,E)-2-(3-pyridyl-methylthio)methyl-4-(4-methoxy-phenoxy)methyl-(1,3)-dioxolane;
(Z,E)-2-(3-pyridyl-methylthio)methyl-4-(2-methoxy-phenoxy)-methyl-(1,3)-thioxolane;
1-(3-pyridyl)-2-thia-4-(4-methoxy-phenoxy)butane;
1-(3-pyridyl)-2-thia-4-(4-acetamido-phenoxy)-butane;
1-(3-pyridyl)-2-thia-4-(4-imidazol-1-yl-phenoxy)butane;
1-(3-pyridyl)-2-thia-4-(2-methoxy-4-allyl-phenoxy)-butane.

EXAMPLE 28

A solution of dicyclohexylcarbodiimide (2.5 g) in DMF (10 ml) is slowly added dropwise to a solution of 3-thia-4-/4-(2-methoxy-phenoxy)methyl-(Z,E)-(1,3)-dioxolan-2-yl/-butanoic acid (3.4 g) and 3-aminomethyl-pyridine (1.08 g) in dimethylformamide (10 ml), cooled at 0° C.

After 30′ at 0° C., the reaction temperature is raised up to room temperature. After 4 hours the mixture is filtered and concentrated to dryness under vacuum; the residue is purified on silica gel column (EtOAc/MeOH=10:1) affording 2.5 g of N-(3-pyridyl)-methyl-3-thia-4-/4-(2-methoxyphenoxy)methyl-(Z,E)-(1,3)-dioxolan-2-yl/-butanoic acid amide.

EXAMPLE 29

By reacting according to example 26 the appropriate carboxylic acids with 3-aminomethyl-pyridine, the following compounds are obtained:

N-(3-pyridyl)methyl-3-thia-5-(2-methoxy-phenoxy) pentanoic acid amide;
N-(3-pyridyl)methyl-3-thia-5-(4-methoxy-phenoxy) pentanoic acid amide;
N-(3-pyridyl)methyl-3-thia-5-(3,4,5-trimethoxy-phenoxy) pentanoic acid amide;
N-(3-pyridyl)methyl-3-thia-4-/4-(2-methoxy-phenoxy)methyl-(Z,E)-(1,3)-dioxolan-2-yl/-butanoic acid amide;
N-(3-pyridyl)methyl-3-thia-4-/4-(4-methoxy-phenoxy)methyl-(Z,E)-(1,3)-dioxolan-2-yl/-butanoic acid amide;
N-(3-pyridyl)methyl-3-thia-4-/2-(2-methoxy-phenoxy)methyl-(Z,E)-(1,3)-dioxolan-3-yl/-butanoic acid amide;
N-(3-pyridyl)methyl-3-oxa-4-/4-(2-methoxy-phenoxy)methyl-(Z,E)-(1,3)-dioxolan-2-yl/-butanoic acid amide.

We claim:

1. Compounds of formula I

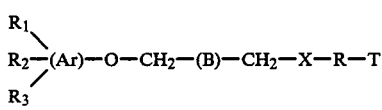

(I)

wherein:

Ar is phenyl;
$R_1$, $R_2$ and $R_3$ are substituents of the phenyl group Ar in 2-, 3-, 4- and 5-position and which can be the same or different and are selected from the group consisting of hydrogen, hydroxy, ($C_1$-$C_5$)-acyloxy, ($C_1$-$C_4$)-alkyl, ($C_1$-$C_4$)-alkoxyl, ($C_2$-$C_4$)-alkenyl, halogen, ($C_1$-$C_5$)-acylamino, phenyl, phenoxy, carboxyl, ($C_1$-$C_3$)-alkoxycarbonyl, carboxy-($C_1$-$C_4$)-alkyl;
B is 1, 3-dioxolan-diyl radical:
X is sulphur or oxygen;
R represents a —($CH_2$)$_n$, —$CH(R_4)$—, a —$CH_2$—$CH(NH_2)$— or —$CH_2$—$CH(NH$—$COR_a$)- group;
T is carboxyl, —$CO_2R_6$, —$COR_6$, —$CO_2NH_2$, —$CONR_dR_e$, —$CO$—$NH$—$CH(R_c)$—$CO_2R_a$ or a di-($C_1$-$C_4$)-alkylamino-($C_1$-$C_4$)-alkylaminocarbonyl, hydroxy-($C_1$-$C_4$)-alkoxy-($C_1$-$C_4$)-alkoxy-($C_1$-$C_4$)-alkylaminocarbonyl, or di-($C_1$-$C_4$)-alkyl-amino-($C_1$-$C_4$)-alkoxy-($C_1$-$C_4$)-alkyl-amino-carbonyl group;
n is 1 or 2;
$R_4$ represents a ($C_1$-$C_4$)-alkyl or a ($C_2$-$C_4$)alkenyl group;
$R_6$ is a ($C_1$-$C_6$)-alkyl group optionally substituted by ($C_1$-$C_6$)-alkyl group optionally substituted by ($C_1$-$C_6$)-alkoxyl, carboxyl, ($C_1$-$C_4$)-alkylamino, di-($C_1$-$C_4$)-alkylamino, ($C_3$-$C_6$)-alkenyl, phenyl, or phenyl-($C_1$-$C_6$)-alkyl groups;
Ra is hydrogen or a $C_1$-$C_4$)-alkyl group and Rc is hydrogen or a ($C_1$-$C_6$)-alkyl, or pyridyl or ($C_6$-$C_{14}$)-ar-($C_1$-$C_4$)-alkyl,
Rd and Re, which can be the same or difference, are hydrogen, a ($C_1$-$C_6$)-alkyl group, optionally substituted by a ($C_1$-$C_6$)-alkoxy, hydroxy-($C_1$-$C_4$)-alkoxy-($C_1$-$C_4$)-alkyl or di-($C_1$-$C_4$)-alkyl-amino-($C_1$-$C_4$)-alkyl-amino-($C_1$-$C_4$)-alkoxy-($C_1$-$C_4$)-alkyl group, or Rd and Re together with the nitrogen atom to which they are bonded form a pyridyl heterocyclic ring, as well as their enantiomers or diastereomers and the pharmaceutically acceptable salts thereof.

2. Compounds according to claim 1 wherein X is oxygen.

3. Compounds according to claim 1 wherein X is sulphur.

4. Compounds according to claim 1, 2 or 3 wherein B is a 1,3-dioxolan-2,4-diyl or 1,3-dioxolan-4,2-diyl.

5. Compounds according to claim 1, 2 or 3 wherein T is carboxyl, ($C_1$-$C_3$)-alkoxycarbonyl, carboxyamide, —$CONR_dR_e$, (3-pyridyl)methylaminocarbonyl, or —$CO$—$NH$—$CH(R_c)$—$CO_2R_a$.

6. Compounds according to claim 1, 2 or 3 wherein $R_1$, $R_2$ and $R_3$ are hydrogen, hydroxy, ($C_1$-$C_4$)-alkyl, ($C_1$-$C_4$)-alkoxy, ($C_2$-$C_4$)-alkenyl, halogen, or ($C_1$-$C_5$)-acylamino.

7. A pharmaceutical composition containing a compound according to any one of claims 1, 2 or 3, and a pharmaceutically acceptable carrier or adjuvant.

8. A method of producing a mucolytic or antitussive effect in a patient in need of such effect, said method comprising administering to said patient a therapeutically effective amount of a compound of claim 1.

* * * * *